US009125829B2

(12) United States Patent
Bonda et al.

(10) Patent No.: US 9,125,829 B2
(45) **Date of Patent: *Sep. 8, 2015**

(54) METHOD OF PHOTOSTABILIZING UV ABSORBERS, PARTICULARLY DIBENZYOLMETHANE DERIVATIVES, E.G., AVOBENZONE, WITH CYANO-CONTAINING FUSED TRICYCLIC COMPOUNDS

(75) Inventors: Craig A. Bonda, Winfield, IL (US); Shengkui Hu, Darien, IL (US)

(73) Assignee: HALLSTAR INNOVATIONS CORP., Chicago, IL (US)

(*) Notice: Subject to any disclaimer, the term of this patent is extended or adjusted under 35 U.S.C. 154(b) by 191 days.

This patent is subject to a terminal disclaimer.

(21) Appl. No.: 13/588,662

(22) Filed: Aug. 17, 2012

(65) Prior Publication Data

US 2014/0050681 A1 Feb. 20, 2014

(51) Int. Cl.

| | |
|---|---|
| ***C07C 255/41*** | (2006.01) |
| ***C07C 69/618*** | (2006.01) |
| ***C07C 335/12*** | (2006.01) |
| ***A61K 8/40*** | (2006.01) |
| ***A61Q 17/04*** | (2006.01) |
| ***A61K 8/49*** | (2006.01) |

(52) U.S. Cl.

CPC . *A61K 8/40* (2013.01); *A61K 8/498* (2013.01); *A61K 8/4986* (2013.01); *A61Q 17/04* (2013.01)

(58) Field of Classification Search

None

See application file for complete search history.

(56) References Cited

U.S. PATENT DOCUMENTS

| | | | |
|---|---|---|---|
| 3,218,166 | A | 11/1965 | Reitter |
| 3,408,187 | A | 10/1968 | Joseph Mammino |
| 3,408,188 | A | 10/1968 | Joseph Mammino |
| 3,408,190 | A | 10/1968 | Joseph Mammino |
| 3,615,412 | A | 10/1971 | Hessel |
| 3,674,473 | A | 7/1972 | Blanchette |
| 3,752,668 | A | 8/1973 | Baltazzi |
| 3,791,824 | A | 2/1974 | Bauer et al. |
| 3,841,871 | A | 10/1974 | Blanchette |
| 3,864,126 | A | 2/1975 | Nishide et al. |
| 3,933,505 | A | 1/1976 | Shiba et al. |
| 3,976,485 | A | 8/1976 | Groner |
| 3,984,378 | A | 10/1976 | Kubota et al. |
| 4,012,251 | A | 3/1977 | Turner |
| 4,018,602 | A | 4/1977 | Chu |
| 4,032,226 | A | 6/1977 | Groner |
| 4,040,735 | A | 8/1977 | Winkelmann et al. |
| 4,069,046 | A | 1/1978 | Hoegl et al. |
| 4,106,934 | A | 8/1978 | Turnblom |
| 4,256,819 | A | 3/1981 | Webster et al. |
| 4,350,748 | A | 9/1982 | Lind |
| 4,427,753 | A | 1/1984 | Fujimura et al. |
| 4,474,865 | A | 10/1984 | Ong et al. |
| 4,515,881 | A | 5/1985 | Sawada et al. |
| 4,546,059 | A | 10/1985 | Ong et al. |
| 4,552,822 | A | 11/1985 | Kazmaier et al. |
| 4,559,287 | A | 12/1985 | McAneney et al. |
| 4,562,132 | A | 12/1985 | Ong et al. |
| 4,567,124 | A | 1/1986 | Ohta et al. |
| 4,576,886 | A | 3/1986 | Hirose et al. |
| 4,579,800 | A | 4/1986 | Hirose et al. |

(Continued)

FOREIGN PATENT DOCUMENTS

| | | |
|---|---|---|
| EP | 0761201 A1 | 3/1997 |
| EP | 0761214 | 3/1997 |

(Continued)

OTHER PUBLICATIONS

Nogami et al., Bull. Chem. Soc. Jpn., 1981, 54(11), pp. 3601-3602.*

(Continued)

*Primary Examiner* — Brian Gulledge

(74) *Attorney, Agent, or Firm* — Baker & McKenzie LLP

(57) ABSTRACT

A photostabilized photoactive composition comprising a mixture of a photoactive compound that develops a singlet excited state, or fluoresces when subjected to UV radiation and an effective amount of an excited state quencher comprising a cyano-containing fused tricyclic compound of formula (I):

(I)

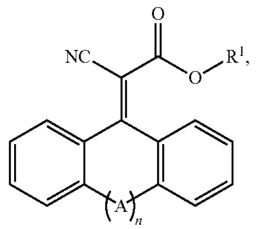

wherein:

A is selected from the group consisting of O, S, C═O, and

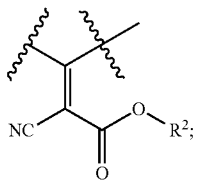

n is selected from the group consisting of 0 and 1; and, $R^1$ and $R^2$ are each independently selected from the group consisting of alkyl, cycloalkyl, ether, aryl, and amino.

56 Claims, 1 Drawing Sheet

(56) References Cited

U.S. PATENT DOCUMENTS

| | | | |
|---|---|---|---|
| 4,599,287 | A | 7/1986 | Fujimaki et al. |
| 4,606,861 | A | 8/1986 | Ong et al. |
| 4,609,602 | A | 9/1986 | Ong et al. |
| 4,810,608 | A | 3/1989 | Ueda |
| 4,820,601 | A | 4/1989 | Ong et al. |
| 4,822,704 | A | 4/1989 | Akasaki et al. |
| 4,833,054 | A | 5/1989 | Akasaki et al. |
| 4,835,081 | A | 5/1989 | Ong et al. |
| 4,842,971 | A | 6/1989 | Sugaiwa et al. |
| 4,845,263 | A | 7/1989 | Ong et al. |
| 4,868,080 | A | 9/1989 | Umehara et al. |
| 4,895,781 | A | 1/1990 | Takai |
| 4,921,769 | A | 5/1990 | Yuh et al. |
| 4,925,757 | A | 5/1990 | Takenouchi et al. |
| 4,942,106 | A | 7/1990 | Takai et al. |
| 4,943,501 | A | 7/1990 | Kinoshita et al. |
| 4,948,911 | A | 8/1990 | Bugner et al. |
| 4,990,634 | A | 2/1991 | Mukai et al. |
| 4,997,737 | A | 3/1991 | Bugner et al. |
| 5,011,757 | A | 4/1991 | Akasaki et al. |
| 5,011,969 | A | 4/1991 | Akasaki et al. |
| 5,017,645 | A | 5/1991 | Ong et al. |
| 5,023,356 | A | 6/1991 | Mukai et al. |
| 5,028,505 | A | 7/1991 | Akasaki et al. |
| 5,034,294 | A | 7/1991 | Go et al. |
| 5,053,302 | A | 10/1991 | Makino et al. |
| 5,075,189 | A | 12/1991 | Ichino et al. |
| 5,075,487 | A | 12/1991 | Akasaki et al. |
| 5,077,164 | A | 12/1991 | Ueda et al. |
| 5,080,991 | A | 1/1992 | Ono et al. |
| 5,102,757 | A | 4/1992 | Akasaki et al. |
| 5,132,190 | A | 7/1992 | Yamada et al. |
| 5,153,085 | A | 10/1992 | Akasaki et al. |
| 5,158,847 | A | 10/1992 | Go et al. |
| 5,166,016 | A | 11/1992 | Badesha et al. |
| 5,168,024 | A | 12/1992 | Yamamoto et al. |
| 5,194,355 | A | 3/1993 | Ohmura et al. |
| 5,213,924 | A | 5/1993 | Sakamoto |
| 5,235,104 | A | 8/1993 | Yamada et al. |
| 5,286,589 | A | 2/1994 | Go et al. |
| 5,308,726 | A | 5/1994 | Hirano et al. |
| 5,324,604 | A | 6/1994 | Bugner et al. |
| 5,336,577 | A | 8/1994 | Spiewak et al. |
| 5,356,746 | A | 10/1994 | Sugiyama et al. |
| 5,389,481 | A | 2/1995 | Saita et al. |
| 5,413,885 | A | 5/1995 | Datta et al. |
| 5,435,991 | A | 7/1995 | Golman et al. |
| 5,437,950 | A | 8/1995 | Yu et al. |
| 5,492,784 | A | 2/1996 | Yoshikawa et al. |
| 5,501,927 | A | 3/1996 | Imai et al. |
| 5,578,405 | A | 11/1996 | Ikegami et al. |
| 5,658,702 | A | 8/1997 | Nukada |
| 5,663,213 | A | 9/1997 | Jones et al. |
| 5,677,095 | A | 10/1997 | Kikuchi et al. |
| 5,698,141 | A | 12/1997 | Kumar |
| 5,698,355 | A | 12/1997 | Imai et al. |
| 5,723,072 | A | 3/1998 | Kumar |
| 5,744,267 | A | 4/1998 | Meerholz et al. |
| 5,780,194 | A | 7/1998 | Katsukawa et al. |
| 5,795,690 | A | 8/1998 | Takegawa et al. |
| 5,834,144 | A | 11/1998 | Kim et al. |
| 5,871,877 | A | 2/1999 | Ong et al. |
| 5,874,193 | A | 2/1999 | Liu et al. |
| 5,916,719 | A | 6/1999 | Kim et al. |
| 5,942,359 | A | 8/1999 | Kinoshita et al. |
| 6,004,724 | A | 12/1999 | Yamato et al. |
| 6,187,493 | B1 | 2/2001 | Katsukawa et al. |
| 6,194,110 | B1 | 2/2001 | Hsiao et al. |
| 6,287,737 | B1 | 9/2001 | Ong et al. |
| 6,322,941 | B1 | 11/2001 | Hsiao et al. |
| 6,465,648 | B1 | 10/2002 | Tadokoro et al. |
| 6,485,886 | B1 | 11/2002 | Yamato et al. |
| 6,544,701 | B2 | 4/2003 | Tadokoro et al. |
| 6,558,851 | B1 | 5/2003 | Fjeldstad et al. |
| 6,586,148 | B1 | 7/2003 | Graham et al. |
| 6,656,650 | B1 | 12/2003 | Lin et al. |
| 6,756,169 | B2 | 6/2004 | Lin et al. |
| 6,770,410 | B2 | 8/2004 | Yu et al. |
| 6,800,274 | B2 | 10/2004 | Bonda et al. |
| 6,806,024 | B1 | 10/2004 | Kura et al. |
| 6,849,367 | B2 | 2/2005 | Shoshi et al. |
| 6,858,363 | B2 | 2/2005 | Belknap et al. |
| 6,890,693 | B2 | 5/2005 | Zhu et al. |
| 6,899,984 | B2 | 5/2005 | Tokarski et al. |
| 6,905,804 | B2 | 6/2005 | Law et al. |
| 6,919,473 | B2 | 7/2005 | Bonda et al. |
| 6,926,887 | B2 | 8/2005 | Bonda et al. |
| 6,946,226 | B2 | 9/2005 | Wu et al. |
| 6,946,227 | B2 | 9/2005 | Lin et al. |
| 6,955,869 | B2 | 10/2005 | Jubran et al. |
| 6,962,692 | B2 | 11/2005 | Bonda et al. |
| 6,964,833 | B2 | 11/2005 | Tokarski et al. |
| 6,991,880 | B2 | 1/2006 | Tong et al. |
| 7,011,917 | B2 | 3/2006 | Jubran et al. |
| 7,029,812 | B2 | 4/2006 | Tokarski et al. |
| 7,037,630 | B2 | 5/2006 | Vong et al. |
| 7,037,632 | B2 | 5/2006 | Jubran et al. |
| 7,045,263 | B2 | 5/2006 | Zhu et al. |
| 7,045,264 | B2 | 5/2006 | Yokota et al. |
| 7,056,632 | B2 | 6/2006 | Ioannidis |
| 7,063,928 | B2 | 6/2006 | Law et al. |
| 7,067,230 | B2 | 6/2006 | Cammack et al. |
| 7,070,892 | B2 | 7/2006 | Bender et al. |
| 7,070,894 | B2 | 7/2006 | Bender et al. |
| 7,078,139 | B2 | 7/2006 | Yokota et al. |
| 7,090,953 | B2 | 8/2006 | Getautis et al. |
| 7,094,510 | B2 | 8/2006 | Jubran et al. |
| 7,115,348 | B2 | 10/2006 | Zhu et al. |
| 7,126,013 | B2 | 10/2006 | Heeney et al. |
| 7,129,012 | B2 | 10/2006 | Sekiya et al. |
| 7,163,771 | B2 | 1/2007 | Ioannidis et al. |
| 7,172,843 | B2 | 2/2007 | Lee et al. |
| 7,175,958 | B2 | 2/2007 | Shoshi et al. |
| 7,183,026 | B2 | 2/2007 | Zhu et al. |
| 7,205,080 | B2 | 4/2007 | Iwasaki et al. |
| 7,223,507 | B2 | 5/2007 | Ioannidis et al. |
| 7,232,633 | B2 | 6/2007 | Qi et al. |
| 7,235,587 | B2 | 6/2007 | Bonda et al. |
| 7,244,541 | B2 | 7/2007 | Tokarski et al. |
| 7,291,431 | B2 | 11/2007 | Tokarski et al. |
| 7,291,432 | B2 | 11/2007 | Lin et al. |
| 7,297,458 | B2 | 11/2007 | Belknap et al. |
| 7,312,007 | B2 | 12/2007 | Lin et al. |
| 7,326,511 | B2 | 2/2008 | Matsumoto et al. |
| 7,354,534 | B2 | 4/2008 | Lee et al. |
| 7,357,919 | B2 | 4/2008 | Candau |
| 7,357,920 | B2 | 4/2008 | Candau |
| 7,390,601 | B2 | 6/2008 | Wu et al. |
| 7,396,622 | B2 | 7/2008 | Nagasaka et al. |
| 7,431,917 | B2 | 10/2008 | Candau |
| 7,491,989 | B2 | 2/2009 | Loutfy et al. |
| 7,501,216 | B2 | 3/2009 | Jubran et al. |
| 7,544,350 | B2 | 6/2009 | Bonda et al. |
| 7,544,453 | B2 | 6/2009 | Freeman et al. |
| 7,560,161 | B2 | 7/2009 | Qi et al. |
| 7,588,702 | B2 | 9/2009 | Bonda et al. |
| 7,592,113 | B2 | 9/2009 | Nagasaka et al. |
| 7,597,825 | B2 | 10/2009 | Bonda et al. |
| 7,745,083 | B2 | 6/2010 | Nagasaka et al. |
| 7,776,614 | B2 | 8/2010 | Bonda |
| 7,799,317 | B2 | 9/2010 | Bonda et al. |
| 7,893,192 | B2 | 2/2011 | Sasaki et al. |
| 7,928,249 | B2 | 4/2011 | Marks et al. |
| 7,981,402 | B2 | 7/2011 | Bonda et al. |
| 8,119,107 | B2 | 2/2012 | Müller et al. |
| 8,236,469 | B2 | 8/2012 | Belknap et al. |
| 2002/0102484 | A1 | 8/2002 | Miyamoto et al. |
| 2003/0211413 | A1 | 11/2003 | Lin et al. |
| 2003/0228534 | A1 | 12/2003 | Zhu |
| 2004/0013960 | A1 | 1/2004 | Lim et al. |
| 2004/0043314 | A1 | 3/2004 | Jubran et al. |
| 2004/0063011 | A1 | 4/2004 | Lin et al. |
| 2004/0242841 | A1 | 12/2004 | Cammack et al. |
| 2005/0089789 | A1 | 4/2005 | Zhu |

(56) References Cited

U.S. PATENT DOCUMENTS

| | | | | |
|---|---|---|---|---|
| 2006/0002869 | A1 | 1/2006 | Bonda et al. | |
| 2006/0142444 | A1 | 6/2006 | Lee et al. | |
| 2006/0210898 | A1 | 9/2006 | Jubran | |
| 2007/0077505 | A1 | 4/2007 | Lin et al. | |
| 2007/0148571 | A1 | 6/2007 | Iwasaki et al. | |
| 2008/0075921 | A1 | 3/2008 | Tateishi | |
| 2008/0193793 | A1 | 8/2008 | Johannes et al. | |
| 2008/0194821 | A1 | 8/2008 | Johannes et al. | |
| 2008/0286693 | A1 | 11/2008 | Matsumoto et al. | |
| 2008/0305417 | A1 | 12/2008 | Sugimura et al. | |
| 2009/0039323 | A1 * | 2/2009 | Bonda et al. | 252/589 |
| 2010/0294368 | A1 | 11/2010 | Ushiro et al. | |
| 2011/0037063 | A1 | 2/2011 | Buesing et al. | |
| 2011/0143273 | A1 | 6/2011 | Sekido et al. | |
| 2012/0121524 | A1 | 5/2012 | Müller et al. | |

FOREIGN PATENT DOCUMENTS

| | | |
|---|---|---|
| EP | 1661548 | 5/2006 |
| JP | H1048554 | 2/1998 |
| JP | 2000-162798 | 6/2000 |
| JP | 2005-139263 | 6/2005 |
| WO | 0061585 | 10/2000 |
| WO | 2004047821 | 6/2004 |
| WO | 2004110394 | 12/2004 |
| WO | 2005048944 | 6/2005 |
| WO | 2006034968 | 4/2006 |
| WO | 2009020673 | 2/2009 |
| WO | WO-2009/020676 A1 | 2/2009 |

OTHER PUBLICATIONS

International Search Report and the Written Opinion of PCT/US2013/054408 dated Dec. 2, 2013.

Nogami, et al., "The Synthesis of New Electron Acceptors, 9,10-bis [cyano(ethoxycarbonyl)methylene]-9,10-dihydroanthracene and 10-[cyano(ethoxycarbonyl)methylene]-9-anthrone." Bulletin of the Chemical society of Japan (1981), 54(11), 3601-2.

Latif, et al., "Cyano esters and malonoitriles. V. Cyano(fluorenyl)acetic esters, hydroxyl nitriles and benzimidazolylacetonitriles." Australian Journal of Chemistry (1977), 30(10), 2263-9.

Hafez, et al., "Carbonyl and thiocarbonyl compounds. V. Synthesis of Newer Unsaturated Nitriles, Carboxylic Acids, and Esters Derived from Xanthene and Thiaxanthene". Journal of Organic Chemistry (1961), 26, 3988-91.

Latif, et al., "Cleavage of Xanthene Ethers. A New Route to 9-substituted Xanthenes". Canadian Journal of Chemistry (1964), 42(7), 1736-40.

Zeid, et al., "Reactions of 4-chloro-9H-xanthene-9-thione with tetrachloro-o-benzoquinone." Liebigs Annlen der Chemie (1984), 1, 196-8.

P.R. Droupadi et al. "Charge Transfer Complexes of Pheophytin A with Nitroaromatics. Electron Transfer from Excited Singlet of Pheophytin A to Nitroaromatics", Photochemistry and Photobiology, vol. 39, No. 2, Feb. 1, 1984, pp. 161-167, XP055072972.

US 8,435,706, 05/2013, Sekido (withdrawn)

* cited by examiner

METHOD OF PHOTOSTABILIZING UV ABSORBERS, PARTICULARLY DIBENZYOLMETHANE DERIVATIVES, E.G., AVOBENZONE, WITH CYANO-CONTAINING FUSED TRICYCLIC COMPOUNDS

The present invention is directed to a method of photostabilizing photolabile UV absorbers, particularly dibenzoylmethane derivatives, such as Avobenzone, with cyano-containing fused tricyclic compounds. More particularly, it has been found that cyano-containing fused tricyclic compounds (CCFTs) quench the singlet and/or triplet excited energy state of photounstable UV absorbers, e.g., dibenzoylmethane derivatives; and/or accept or donate an electron from or to UV absorbers, thereby returning photolabile UV absorbers, such as dibenzoylmethane derivatives, back to their ground state so that they can absorb more photons, e.g., from ultraviolet light, thereby photostabilizing the dibenzoylmethane derivatives, particularly butylmethoxy dibenzoylmethane (Avobenzone) in photoactive sunscreen, cosmetic and dermatological compositions. When a photolabile UV absorber, such as dibenzoylmethane derivative is excited to a singlet and/or triplet excited state and is contacted with a cyano-containing fused tricyclic compound (CCFT), regardless of the mechanism, the excited dibenzoylmethane derivative is returned to its ground state so that it can absorb more UV radiation, thereby protecting the skin for longer durations.

BACKGROUND AND PRIOR ART

Dibenzoylmethane derivatives are compounds that absorb the full spectrum of UVA radiation. The absorption of UVA radiation (at 320-400 nm) by a dibenzoylmethane derivative causes the excitation of an electron in the dibenzoylmethane derivative molecule from an initially occupied, lower energy orbital to a higher energy, previously unoccupied orbital. The energy of the absorbed photon is used to energize an electron and cause it to "jump" to a higher energy orbital. See Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the UV absorbing molecule, e.g., dibenzoylmethane derivative, is prone to degrade via a number of known pathways and, therefore, can absorb little or no additional UV light. To photostabilize an electronically excited, chromophore-containing, UV absorbing organic molecule in order to provide sufficient UV protection, it must be returned to the ground state before it undergoes a photochemical reaction destructive to its UV absorbing capability.

There are known photostabilizing sunscreen additives, such as Octocrylene, methylbenzylidene camphor, and the esters or polyesters of naphthalene dicarboxylic acid of this assignee's U.S. Pat. Nos. 6,113,931; 6,284,916; 6,518,451; and 6,551,605, all hereby incorporated by reference, that are capable of quenching excited triplet state energy from dibenzoylmethane derivatives. Surprisingly, it has been found that cyano-containing fused tricyclic compounds return chromophore-containing organic molecules, particularly butyl methoxydibenzoylmethane (Avobenzone), octyl methoxycinnamate (Octinoxate), and octyl salicylate (Octisalate), from either an electronically excited singlet state or excited triplet state back to their ground state, thereby photostabilizing the UV-absorbing organic molecules.

Deflandre U.S. Pat. No. 5,576,354 generally discloses a cosmetic sunscreen composition containing at least 1% by weight of an α-cyano-β,β-diphenylacrylate that will photostabilize a dibenzoylmethane derivative, e.g., Parsol 1789 (Avobenzone), so long as the composition contains a fatty phase, e.g., glycerol stearates, isopropyl myristate or the like, and so long as the mole ratio of the α-cyano-β,β-diphenylacrylate to the dibenzoylmethane derivative is at least 0.8.

Octocrylene is known to quench (accept) the excited triplet state energy of an excited photoactive compound by dissipating the energy kinetically in the form of rapid isomerizations. This process is shown below:

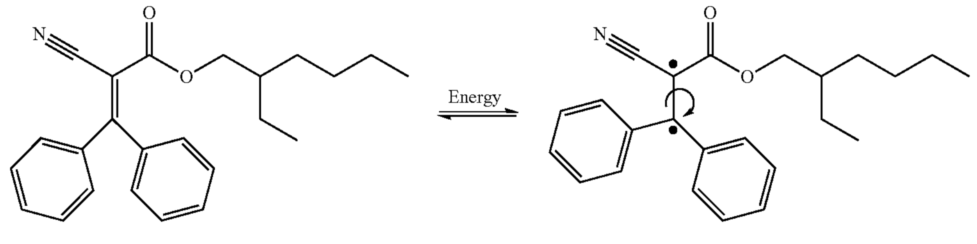

A A* wherein the α-cyano-β,β-diphenylacrylate compound (octocrylene shown above as structure A), accepts the triplet excited state energy from a photoactive compound and forms a diradical (shown above as structure A*) at the α and β positions of the acrylate, which converts the double bond into a single bond and allows for the free rotation of the phenyl groups. This rotation occurs rapidly and efficiently to dissipate any excited triplet state energy accepted by the α-cyano-β,β-diphenylacrylate compound from the photoactive compound.

While octocrylene is able to quench (accept) the triplet excited state energy from a photoactive compound, thereby photostabilizing, to some degree, dibenzoylmethane derivatives, as shown in examples 1, 4, 6 and 8 of Deflandre et al. U.S. Pat. No. 5,576,354, there exists a need in the photoactive composition art to find one or more compounds that quench (accept) the singlet excited state energy and preferably also the triplet excited state energy from photoactive compounds, which octocrylene does not.

Quite surprisingly, it has been found that the cyano-containing fused tricyclic compounds described herein will quench excited state energy of UV-absorbing organic molecules, such as dibenzoylmethane derivatives, particularly Avobenzone, returning the excited UV-absorbing organic molecules to their ground state for additional UV absorption.

SUMMARY

The electronic excited state energy—singlet state and/or triplet state energy from a UV-absorbing molecule, particularly a dibenzoylmethane derivative, such as Avobenzone, has been found to be readily quenched by contact with a cyano-containing fused tricyclic compound.

In one aspect, the disclosure provides a method of quenching excited state energy from a chromophore compound, particularly a dibenzoylmethane derivative, that has been excited by exposure to and absorption of UV radiation comprising quenching the excited state energy of an excited chromophore, UV absorbing compound with a cyano-containing fused tricyclic compound of Formula I:

(I)

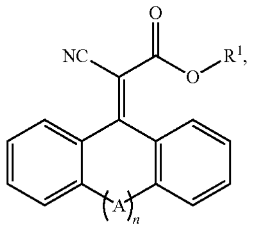

wherein:

A is selected from the group consisting of O, S, C═O, and

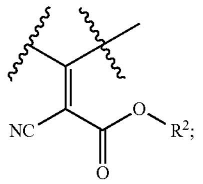

n is selected from the group consisting of 0 and 1; and, $R^1$ and $R^2$ are each independently selected from the group consisting of alkyl, cycloalkyl, ether, aryl, and amino.

In another aspect, the invention provides a sunscreen, cosmetic or dermatological composition for coating a skin surface to protect the skin from absorbing damaging amounts of UV radiation when skin is exposed to sunlight, or other UV radiation, said composition containing a compound of Formula Ia, Ib, Ic, Id, Ie, or a combination thereof:

Formula Ia

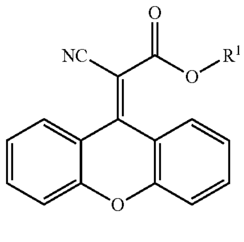

-continued

Formula Ib

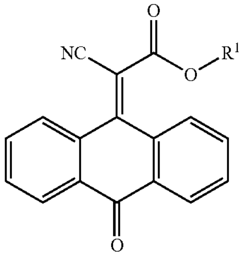

Formula Ic

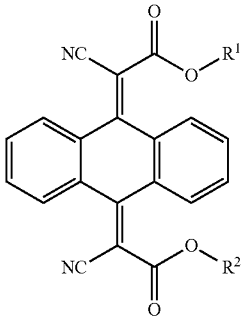

Formula Id

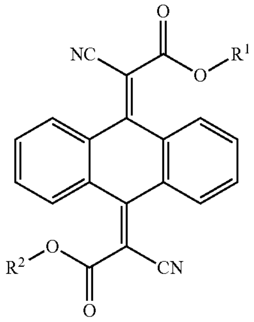

Formula Ie

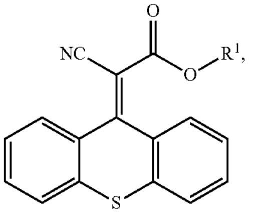

wherein $R^1$ and $R^2$ are each independently selected from the group consisting of alkyl, cycloalkyl, ether, aryl, and amino.

DETAILED DESCRIPTION OF THE PREFERRED EMBODIMENTS

Figure 1:
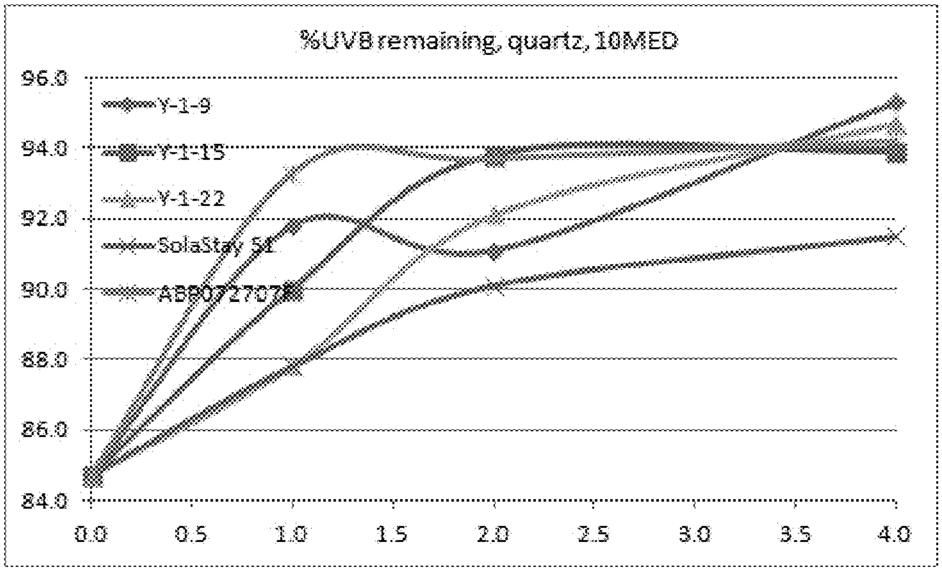
FIG. 1 is a graph showing the superior ability of cyano-containing fused tricyclic compounds to photostabilize Avobenzone in comparison to the ethylhexyl methoxycrylene of this Assignee's U.S. Pat. Nos. 8,075,808; 7,754,191; 7,173,519; 7,597,825; 7,588,702; and 7,959,834; and U.S. Patent Application No. 2009/0246157.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Quite surprisingly, it has been found that cyano-containing fused tricyclic compounds will quench electronically excited UV-absorbing chromophore molecules, particularly dibenzoylmethane derivatives, caused by the chromophore molecule reaching an excited singlet and/or triplet state when excited by absorption of UV radiation. As a result, the excited state of the chromophore-containing molecules, particularly Avobenzone, is returned to the ground state, thereby photostabilizing the chromophore-containing molecule so that it can absorb additional UV radiation. Accordingly, by applying one or more of the cyano-containing fused tricyclic compounds, in a dermatologically or cosmetically acceptable carrier, onto mammalian skin, e.g., human skin, the skin will not be damaged as a result of the UV absorbing molecule being unable to absorb additional UV radiation. Thus, the compositions and methods described herein advantageously quench the excited states reached by chromophore-containing compounds, particularly dibenzoylmethane derivatives, thereby photostabilizing the UV-absorbing molecules to allow them to absorb additional UV radiation.

DEFINITIONS

The term "alkyl" refers to straight chained and branched saturated hydrocarbon groups containing one to thirty carbon atoms, for example, one to thirty carbon atoms, one to twenty carbon atoms, and/or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl groups having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. When the term "alkyl" is in parenthesis (e.g., (alkyl)acrylate), then the alkyl group is optional.

The term "alkenyl" is defined identically as "alkyl" except for containing at least one carbon-carbon double bond, e.g., ethenyl, 1-propenyl, 2-propenyl, and butenyl. Unless otherwise indicated, an alkenyl group can be an unsubstituted alkenyl group or a substituted alkenyl group.

The term "alkynyl" is defined identically as "alkyl" except for containing at least one carbon-carbon triple bond, e.g., ethynyl, 1-propynyl, 2-propynyl, and butynyl. Unless otherwise indicated, an alkynyl group can be an unsubstituted alkynyl group or a substituted alkynyl group.

The term "cycloalkyl" as used herein refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

The term "heterocycloalkyl is defined similarly as cycloalkyl, except the ring contains one to three heteroatoms independently selected from the group consisting of oxygen, nitrogen, and sulfur. Nonlimiting examples of heterocycloalkyl groups include piperidine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, $C(O)NH_2$, $NH_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

The term "cycloalkenyl" is defined identically as "cycloalkyl" except for containing at least one double bond, e.g., cyclobutenyl, cyclopentenyl, cyclohexenyl, cycloheptenyl, and cyclooctenyl. Unless otherwise indicated, a cycloalkenyl group can be an unsubstituted cycloalkenyl group or a substituted cycloalkenyl group.

The term "aryl" as used herein refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, and fluorenyl. Unless otherwise indicated, an aryl group can be an unsubstituted aryl group or a substituted aryl group.

The term "heteroaryl" as used herein refers to monocyclic or polycyclic (e.g., fused bicyclic and fused tricyclic) aromatic ring systems, wherein one to four-ring atoms are selected from the group consisting of oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

The term "hydroxy" or "hydroxyl" as used herein refers to an "—OH" group.

The term "alkoxy" or "alkoxyl" as used herein refers to an "–O-alkyl" group.

The term "ester" as used herein refers to a group of the general Formula:

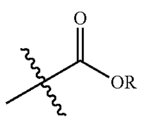

wherein R is an alkyl group or a cycloalkyl group.

The term "ether" as used herein refers to a $C_1$-$C_{30}$ alkyl group that includes at least one oxygen atom inserted within the alkyl group.

The term "amino" as used herein refers a —$NH_2$ or —NH— group, wherein each hydrogen in each Formula can be replaced with an alkyl, cycloalkyl, aryl, heteroaryl, or heterocycloalkyl group.

The term "carboxy" or "carboxyl" as used herein refers to a "—COOH" group.

The term "carboxylic ester" as used herein refers to a "—(C═O)O-alkyl" group.

The term "sulfhydryl" as used herein refers to a "—SH" group.

The term "halo" as used herein refers to a halogen (e.g., F, Cl, Br, or I).

The term "cyano" as used herein refers to a —C≡N group, also designated —CN.

A "substituted" alkyl, alkenyl, alkynyl, cycloalkyl, cycloalkenyl, aryl, heteroaryl, alkoxyl, ester, ether, or carboxylic ester refers to an alkyl, alkenyl, alkynyl, cycloalkyl, cycloalkenyl, aryl, heteroaryl, alkoxyl, ester, ether, or carboxylic ester having at least one hydrogen radical that is substituted with a non-hydrogen radical (i.e., a substitutent). Examples of non-hydrogen radicals (or substituents) include, but are not limited to, alkyl, cycloalkyl, alkenyl, cycloalkenyl, alkynyl, ether, aryl, heteroaryl, heterocycloalkyl, heterocycloalkyl, hydroxyl, oxy (or oxo), alkoxyl, ester, thioester, acyl, carboxyl, cyano, nitro, amino, amido, sulfur, and halo. When a substituted alkyl group includes more than one non-hydrogen radical, the substituents can be bound to the same carbon or two or more different carbon atoms.

The term "hydroxyalkyl" as used herein refers to an alkyl group that is substituted with a hydroxyl group.

The term "carboxyalkyl" as used herein refers to an alkyl group that is substituted with a carboxyl group.

The term "esteralkyl" as used herein refers to an alkyl group that is substituted with an ester group.

The term "sulfhydrylalkyl" as used herein refers to an alkyl group that is substituted with a sulfhydryl group.

EMBODIMENTS

In one aspect, the disclosure provides a method of quenching excited state energy from a chromophore compound, particularly a dibenzoylmethane derivative, that has been excited by exposure to and absorption of UV radiation, by a cyano-containing fused tricyclic compound.

In one embodiment, the chromophore compound is a dibenzoylmethane derivative, which has its singlet and triplet excited states quenched by cyano-containing, fused tricyclic compounds. The dibenzoylmethane derivative may be selected from the group consisting of 2-methyldibenzoylmethane; 4-methyldibenzoylmethane; 4-isopropyldibenzoylmethane; 4-tert-butyldibenzoylmethane; 2,4-dimethydibenzoylmethane; 2-5-dimethydibenzoylmethane; 4,4'-diispropyldibenzoylmethane; 4,4'-dimethoxydibenzoylmethane; 4-tert-butyl-4'-methoxdibenzoylmethane; 2-methyl-5-isopropy-4'-methoxydibenzoylmethane; 2-methyl-5-tert-butyl-4'-methoxydibenzoylmethane; 2,4-dimethyl-4'-methoxydibenzoymethane; 2,6-dimethyl-4-tert-butyl-4'-methoxydibenzolmthane, and combinations thereof.

In other embodiments, the cyano-containing fused tricyclic compounds described herein also photostabilize retinoids, coenzyme Q, cholecalciferol, and resveratrol, disclosed in this assignee's U.S. Pat. No. 8,070,989, and U.S. Patent Application Publication Nos. 2012/0114572, 2012/0107255, 2012/0065232, 2011/0251242, and 2011/0142771, hereby incorporated by reference.

In yet other embodiments, the cyano-containing fused tricyclic compounds described herein photostablize porphyrin compounds. Porphyrin compounds that are useful in the present invention include, but are not limited to, 5-azaprotoporphyrin IX, bis-porphyrin, coproporphyrin III, deuteroporphyrin, deuteroporphyrin IX dichloride, diformyl deuteroprophyrin IX, dodecaphenylporphyrin, hematoporphyrin, hematoporphyrin IX, hematoporphyrin monomer, hematoporphyrin dimer, hematoporphyrin derivative, hematoporphyrin derivative A, hematoporphyrin IX dihydrochloride, hematoporphyrin dihydrochloride, mesoporphyrin, mesoporphyrin IX, monohydroxyethylvinyl deuteroporphyrin, 5,10,15,20-tetra(o-hydroxyphenyl)porphyrin, 5,10,15,20-tetra(m-hydroxyphenyl)porphyrin, 5,10,15,20-tetra(p-hydroxyphenyl)porphyrin, 5,10,15,20-tetrakis(3-methoxyphenyl)-porphyrin, 5,10,15,20-tetrakis(3,4-dimethoxyphenyl)porphyrin, 5,10,15,20-tetrakis(3,5-dimethoxyphenyl)porphyrin, 5,10,15,20-tetrakis(3,4,5-trimethoxyphenyl)porphyrin, 2,3,7,8,12,13,17,18-octaethyl-5,10,15,20-tetraphenylporphyrin, porphyrin c, protoporphyrin, protoporphyrin IX, tetra-(4-N-carboxyphenyl)-porphine, tetra-(3-methoxyphenyl)-porphine, tetra-(3-methoxy-2,4-difluorophenyl)-porphine, 5,10,15,20-tetrakis(4-N-methylpyridyl)porphine, tetra-(4-N-methylpyridyl)-porphine tetrachloride, tetra-(3-N-methylpyridyl)-porphine, tetra-(2-N-methylpyridyl)-porphine, tetra(4-N,N,N-trimethylanilinium)porphine, tetra-(4-N,N,N"-trimethylaminophenyl)porphine tetrachloride, tetranaphthaloporphyrin, tetraphenylporphyrin, tetra-(4-sulfonatophenyl)-porphine, 4-sulfonatophenylporphine, uroporphyrin, uroporphyrin III, uroporphyrin IX, and uroporphyrin I, and esters thereof.

The cyano-containing fused tricyclic compounds capable of quenching the excited state energy of the UV-absorbing compounds, particularly dibenzoylmethane derivatives, are the compounds of Formula I:

Formula I

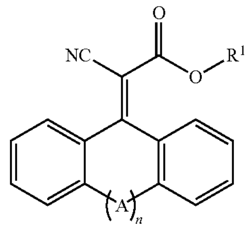

Cyano-Containing Fused Tricyclic Compounds wherein:

A is selected from the group consisting of O, S, C═O, and

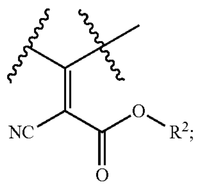

n is 0 or 1; and, $R^1$ and $R^2$ are each independently alkyl, cycloalkyl, ether, aryl, or amino.

In some embodiments, the compounds of Formula I include the compounds of Formula Ia, Ib, Ic, Id, Ie, and If:

Formula Ia

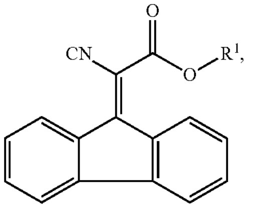

Formula Ib

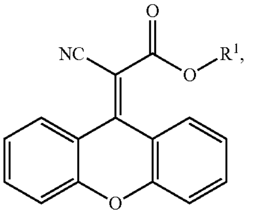

Formula Ic

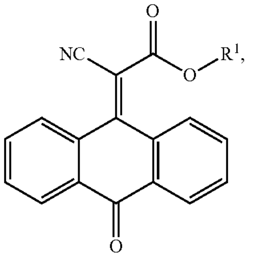

Formula Id

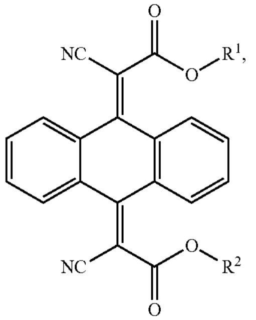

Formula Ie

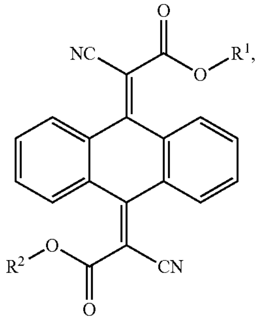

Formula If

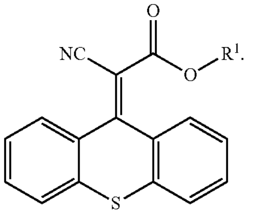

In some embodiments, $R^1$ is $C_1$-$C_{30}$ alkyl, $C_1$-$C_{20}$ alkyl, or $C_1$-$C_{10}$ alkyl. For example, $R^1$ can include, but is not limited to, methyl, ethyl, propyl, isopropyl, or 2-ethylhexyl.

In some embodiments, $R^2$ is $C_1$-$C_{30}$ alkyl, $C_1$-$C_{20}$ alkyl, or $C_1$-$C_{10}$ alkyl. For example, $R^2$ can include, but is not limited to, methyl, ethyl, propyl, isopropyl, or 2-ethylhexyl.

In some exemplary embodiments, the compounds of Formula I are selected from the group consisting of:

Formula Iai

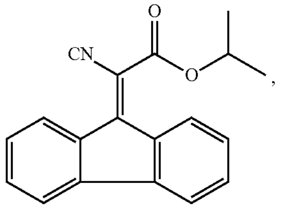

Formula Ibi

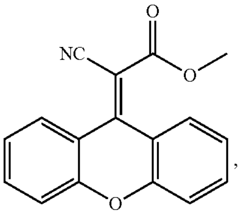

Formula Ici

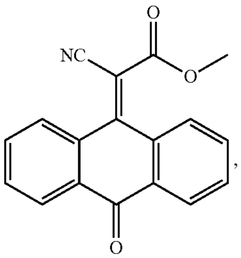

Formula Idi

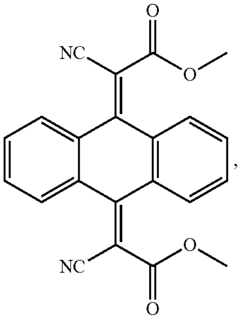

Formula Iei

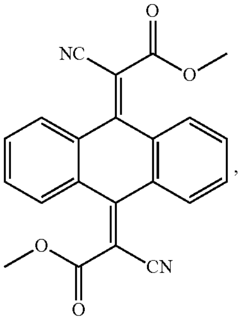

and

-continued

Formula Ifi

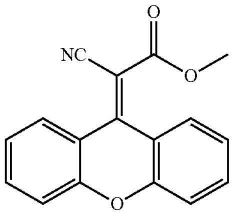

In accordance with one important embodiment, a cyano-containing fused tricyclic compound of Formula I, Ia, Iai, Ib, Ibi, Ic, Ici, Id, Idi, Ie, Iei, If, Ifi, or a combination thereof is included in a sunscreen, cosmetic or dermatological composition for coating a skin surface to protect the skin from UV damage when exposed to sunlight, or other UV radiation. In preferred embodiments, the sunscreen, cosmetic or dermatological composition includes a UVA filter and/or a UVB filter compound and/or a broad-band filter compound, particularly a dibenzoylmethane derivative UVA filter that is photostabilized by the cyano-containing fused tricyclic compound for protection of the skin from UVA and/or UVB wavelengths.

The cyano-containing fused tricyclic compound of Formula I can be included in the sunscreen, cosmetic or dermatological composition in an amount of about 0.01% by weight to about 20% by weight, preferably from about 0.1 to about 20% by weight, more preferably from about 0.1% to about 10% by weight, in each case based on the total weight of the composition.

The total amount of one or more water-soluble UV filter substances in the finished sunscreen, cosmetic, or dermatological preparations is advantageously chosen from the range 0.01% by weight to about 20% by weight, preferably from about 0.1 to about 20% by weight, more preferably from about 0.1% to about 10% by weight, in each case based on the total weight of the composition.

Preferred UV filter compounds are disclosed in published PCT application WO 2009/020676, hereby incorporated by reference for preferred water-soluble, organic and particulate UV filter compounds.

In a preferred embodiment, the sunscreen, cosmetic or dermatological compositions described herein contain one or more of the cyano-containing fused tricyclic compounds as well as one or more UV-absorbing, chromophore-containing compounds. The compositions preferably include both UV-A and UV-B photoactive compounds in a cosmetically acceptable carrier, optionally including additives, such as emollients, stabilizers, emulsifiers, and combinations thereof. These additives can be used in preparing a UV filter composition in an emulsion (oil-in-water or water-in-oil) from a composition that includes one or more photoactive compounds and a solvent or a solvent combination that includes one or more organic solvents and water. When made, preferably the emulsion is an oil-in-water emulsion, wherein the oil phase is primarily formed from a mixture of the UV filter compound(s), preferably including a dibenzoylmethane derivative, such as Avobenzone, and one or more organic solvents.

A typical photoactive composition includes one or more photoactive compounds, wherein the photoactive compound(s) act to absorb UV radiation and thereby protect the substrate (e.g., human skin, resins, films, and the like) from the harmful effects of UV radiation. The absorption process causes a photoactive compound to reach an excited state, wherein the excited state is characterized by the presence of excited electronic energy (e.g., singlet state energy or triplet state energy), as compared to the ground state of the photoactive compound. Once a photoactive compound reaches an excited state there exists a number of pathways by which the excited photoactive compound can dissipate its excess energy (e.g., singlet and/or triplet energy), however, many of those pathways adversely affect the ability of the photoactive compound to further absorb UV radiation. The cyano-containing fused tricyclic molecules described herein accept electronic singlet excited state energy from UV-absorbers, particularly Avobenzone, octyl methoxycinnamate (Octinoxate), and octyl salicylate (Octisalate). The cyano-containing fused tricyclic compounds also are very effective UVA absorbers in addition to providing electronic singlet state energy quenching of other UV-absorbing compounds in sunscreen, cosmetic and dermatological compositions. The cyano-containing fused tricyclic molecules described herein are especially effective when combined with one or more additional electronic singlet excited state quenching compounds such as oxybenzone and/or any of the alkoxy crylene disclosed in this assignee's U.S. Pat. Nos. 8,075,808; 7,754,191; 7,173,519; 7,597,825; 7,588,702; and 7,959,834; and U.S. Patent Application No. 2009/0246157, hereby incorporated by reference. Particularly surprising photostabilization is achieved in sunscreen compositions containing the cyano-containing fused tricyclic molecules described herein together with octyl methoxycinnamate and Avobenzone.

A photoactive compound is one that responds to light photoelectrically. In the compositions and methods of photostabilization disclosed herein, a photoactive compound is one that responds to UV radiation photoelectrically. For example, all photoactive compound-containing compositions that respond to UV radiation photoelectrically by photoactive compound photodegradation benefit highly by the inclusion of the cyano-containing fused tricyclicmolecules described herein. The cyano-containing fused tricyclic compounds described herein are useful photostabilizers and/or photoactive compounds when combined with any single or combination of photoactive compounds identified in Shaath, Nadim, Encyclopedia of UV filters, © 2007, hereby incorporated by reference. Photostability is a problem with all UV filters because they all reach an electronic singlet excited state upon exposure to UV radiation.

It is theorized that the following UV filters are photostabilized by the cyano-containing fused tricyclic molecules described herein, including all of the following, including combinations of any two or more, and include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; n- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoylmethane, butylmethoxydibenzoylmethane, etocrylene, and 4-isopropyldibenzoylmethane).

The following UV filters should be particularly photostabilized by the cyano-containing fused tricyclic molecules described herein: 2-ethylhexyl p-methoxycinnamate, 4,4'-t-butyl methoxydibenzoylmethane, octyldimethyl p-aminobenzoate, digalloyltrioleate, ethyl 4-[bis(hydroxypropyl)] aminobenzoate, 2-ethylhexylsalicylate, glycerol p-aminobenzoate, 3,3,5-trimethylcyclohexylsalicylate, and combinations thereof.

Photoactive compositions disclosed herein can include a variety of photoactive compounds, preferably including one or more UV-A photoactive compounds and one or more UV-B photoactive compounds. Preferably, a sunscreen composition includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; uric acid derivatives; vilouric acid derivatives; tannic acid and derivatives thereof; hydroquinone; diethylamino hydroxybenzoyl hexyl benzoate and salts and derivatives thereof; and combinations of the foregoing.

UV A radiation (about 320 nm to about 400 nm), is recognized as contributing to causing damage to skin, particularly to very lightly colored or sensitive skin. A sunscreen composition disclosed herein preferably includes a UV-A photoactive compound. Preferably, a sunscreen composition disclosed herein includes a dibenzoylmethane derivative UV-A photoactive compound. Preferred UV-A absorbing dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

For a product marketed in the United States, preferred cosmetically acceptable photoactive compounds and concentrations (reported as a percentage by weight of the total cosmetic sunscreen composition) include: aminobenzoic acid (also called para aminobenzoic acid and PABA; 15% or less), Avobenzone (also called butyl methoxy dibenzoylmethane; 3% or less), cinoxate (also called 2 ethoxyethyl p methoxycinnamate; 3% or less), dioxybenzone (also called benzophenone 8; 3% or less), homosalate ((also called 3,3,5-trimethylcyclohexyl salicylate, 15% or less), menthyl anthranilate (also called menthyl 2 aminobenzoate; 5% or less), octocrylene (also called 2 ethylhexyl 2 cyano 3,3 diphenylacrylate; 10% or less), octyl methoxycinnamate (7.5% or less), octyl salicylate (also called 2 ethylhexyl salicylate; 5% or less), oxybenzone (also called benzophenone 3; 6% or less), padimate 0 (also called octyl dimethyl PABA; 8% or less), phenylbenzimidazole sulfonic acid (water soluble; 4% or less), sulisobenzone (also called benzophenone 4; 10% or less), titanium dioxide (25% or less), trolamine salicylate (also called triethanolamine salicylate; 12% or less), and zinc oxide (25% or less).

Other preferred cosmetically acceptable photoactive compounds and preferred concentrations (percent by weight of the total cosmetic sunscreen composition) include diethanolamine methoxycinnamate (10% or less), ethyl-[bis(hydroxypropyl)]aminobenzoate (5% or less), glyceryl aminobenzoate (3% or less), 4 isopropyl dibenzoylmethane (5% or less), 4 methylbenzylidene camphor (6% or less), terephthalylidene dicamphor sulfonic acid (10% or less), and sulisobenzone (also called benzophenone 4, 10% or less).

For a product marketed in the European Union, preferred cosmetically acceptable photoactive compounds and preferred concentrations (reported as a percentage by weight of the total cosmetic sunscreen composition) include: PABA (5% or less), camphor benzalkonium methosulfate (6% or less), homosalate (10% or less), benzophenone 3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG 25 PABA (10% or less), isoamyl p methoxycinnamate (10% or less), ethylhexyl triazone (5% or less), drometrizole trielloxane (15% or less), diethylhexyl butamido triazone (10% or less), 4 methylbenzylidene camphor (4% or less), 3 benzylidene camphor (2% or less), ethylhexyl salicylate (5% or less), ethylhexyl dimethyl PABA (8% or less), benzophenone 4 (5%, expressed as acid), methylene bis benztriazolyl tetramethylbutylphenol (10% or less), disodium phenyl dibenzimidazole tetrasulfonate (10% or less, expressed as acid), bis ethylhexyloxyphenol methoxyphenol triazine (10% or less), methylene bisbenzotriazolyl tetramethylbutylphenol (10% or less, also called TINOSORB M or Bisoctrizole), and bisethylhexyloxyphenol methoxyphenyl triazine. (10% or less, also called TINOSORB S or Bemotrizinol).

All of the above described UV filters are commercially available. For example, suitable commercially available organic UV filters are identified by trade name and supplier in Table I below:

TABLE I

| CTFA Name | Trade Name | Supplier |
|---|---|---|
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| diethylamino hydroxybenzoyl hexyl benzoate | UVINUL A-PLUS | BASF Chemical Co. |
| diethylhexyl butamido triazone | UVISORB HEB | 3V-Sigma |
| disodium phenyl dibenzylimidazole | NEO HELIOPAN AP | Symrise |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

Commonly-assigned U.S. Pat. Nos. 6,485,713 and 6,537,529, the disclosures of which are hereby incorporated herein by reference, describe compositions and methods for increasing the photostability of photoactive compounds in a sunscreen composition, e.g., by the addition of polar solvents to the oil phase of a composition. By increasing the polarity of the oil phase of a sunscreen composition including the alkoxy crylenes described herein, e.g., methoxy crylene, the stability of the sunscreen composition is surprisingly increased in comparison to octocrylene. In the sunscreen compositions described herein, preferably, one or more of a highly polar solvent is present in the oil-phase of the composition. Preferably, a sufficient amount of a polar solvent is present in the sunscreen composition to raise the dielectric constant of the oil-phase of the composition to a dielectric constant of at least about 7, preferably at least about 8. With or without the highly polar solvent in the oil phase, the methoxy crylene molecules described herein yield unexpected photostability in comparison to octocrylene.

A photoactive compound can be considered stable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 350-370 nm for Avobenzone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compound).

In accordance with one important embodiment, a cyano-containing fused tricyclic compound formula (I) is combined in a sunscreen, cosmetic or dermatological formulation with a water soluble UV filter compound and/or a broad-band filter compound and optionally, but preferably, together with a dibenzoylmethane derivative and/or a dialkyl naphthalate.

Advantageous water-soluble UV filter substances for the purposes of the present invention are sulfonated UV filters, in particular:

phenylene-1,4-bis(2-benzimidazyl)-3,3'-5,5'-tetrasulfonic acid, which has the following structure:

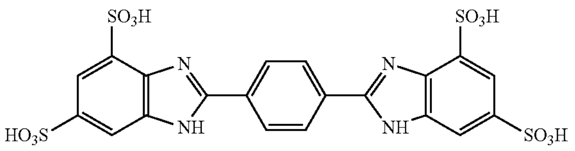 [SMILES: O=S(=O)(O)c1cc(S(=O)(=O)O)c2nc(-c3ccc(-c4nc5c(S(=O)(=O)O)cc(S(=O)(=O)O)cc5[nH]4)cc3)[nH]c2c1]

and its salts, especially the corresponding sodium, potassium or triethanolammonium salts, in particular phenylene-1,4-bis(2-benzimidazyl)-1-3,3'-5,5'-tetrasulfonic acid bissodium salt

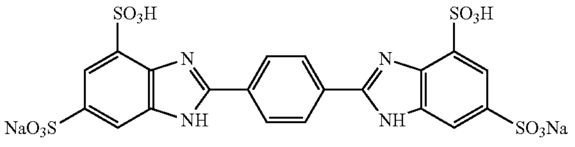

with the INCI name disodium phenyl dibenzimidazole tetrasulfonate (CAS No.: 180898-37-7), which is obtainable for example under the proprietary name Neo Heliopan A P from Haarmann & Reimer.

Further advantageous sulfonated UV filters for the purposes of the present invention are the salts of 2-phenylbenzimidazole-5-sulfonic acid, such as its sodium, potassium or its triethanolammonium salts, and the sulfonic acid itself

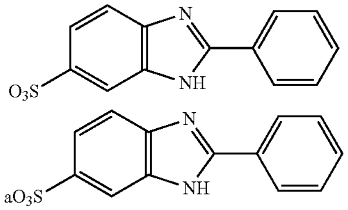

with the INCI name phenylbenzimidazole sulfonic acid (CAS No. 27503-81-7), which is obtainable for example under the proprietary name Eusolex 232 from Merck or under Neo Heliopan Hydro from Haarmann & Reimer.

Further advantageous water-soluble UV-B and/or broad-band filter substances for the purposes of the present invention are, for example, sulfonic acid derivatives of 3-benzylidenecamphor, such as, for example, 4-(2-oxo-3-bornylidenemethyl)benzene-sulfonic acid, 2-methyl-5-(2-oxo-3-bornylidenemethyl)sulfonic acid and the salts thereof.

The total amount of one or more water-soluble UV filter substances in the finished cosmetic or dermatological preparations is advantageously chosen from the range 0.01% by weight to 20% by weight, preferably from 0.1 to 10% by weight, in each case based on the total weight of the preparations.

In accordance with another important embodiment, a cyano-containing fused tricyclic of formula (I), Ia, Iai, Ib, Ibi, Ic, Ici, Id, Idi, Ie, Idi, If, and/or Ifi is combined in a sunscreen, cosmetic or dermatological formulation with a hydroxybenzophenone compound and/or a broad-band filter compound and optionally, but preferably, together with a dibenzoylmethane derivative and/or a dialkyl naphthalate.

With a cyano-containing fused tricyclic compound, it is possible to completely dispense with the use of other UV photostabilizers, in particular the use of ethylhexyl-2-cyano-3,3-diphenylacrylate(octocrylene) or 4-methylbenzylidenecamphor.

Hydroxybenzophenones are characterized by the following structural formula:

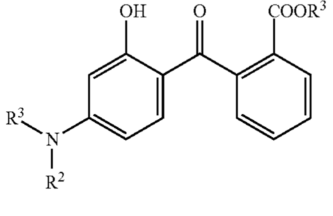

where $R^1$ and $R^2$ independent of one another are hydrogen, $C_1C_{20}$-alkyl, $C_3$-$C_{10}$-cycloalkyl or $C_3$-$C_{10}$-cycloalkenyl, wherein the substituents $R^1$ and $R^2$ together with the nitrogen atom to which they are bound can form a 5- or 6-ring and $R^3$ is a $C_1$-$C_{20}$ alkyl radical.

A particularly advantageous hydroxybenzophenone is the 2-(4'-diethylamino-2'-hydroxybenzoyl)benzoic acid hexyl ester (also: aminobenzophenone) which is characterized by the following structure:

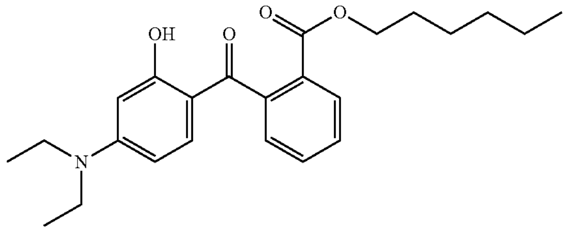 [SMILES: CCCCCCOC(=O)c1ccccc1C(=O)c1ccc(N(CC)CC)cc1O]

and is available from BASF under the Uvinul A Plus.

According to one embodiment of the invention, sunscreen, cosmetic or dermatological preparations contain 0.1 to 20% by weight, advantageously 0.1 to 15% by weight, very particularly preferred 0.1 to 10% by weight, of one or more hydroxybenzophenones.

Within the scope of the present invention, dialkyl naphthalates for which $R^1$ and/or $R^2$ represent branched alkyl groups with 6 to 10 carbon atoms are advantageous. Within the scope of the present invention diethylhexyl naphthalate is very particularly preferred which is available, e.g., under the trade name Hallbrite TQ™ from HallStar Innovaction Corp. or Corapan TQ™ from H&R.

According to one embodiment of the invention, sunscreen, cosmetic or dermatological preparations advantageously contain 0.001 to 30% by weight, preferably 0.01 to 20% by weight, very particularly preferred 0.5 to 15% by weight, of one or more dialkyl naphthalates.

The cosmetic or dermatological light-protection formulations described herein can be composed as usual and be used for sunscreen, cosmetic or dermatological light-protection, furthermore for the treatment, care and cleansing of the skin and/or hair and as a cosmetic product in decorative cosmetics.

In accordance with another important embodiment, cyano-containing fused tricyclic compound is combined in a sunscreen, cosmetic or dermatological formulation with a benzotriazole derivative compound and/or a broad-band filter compound and optionally, but preferably, together with a dibenzoylmethane derivative and/or a dialkyl naphthalate.

An advantageous benzotriazole derivative is 2,2'-methylenebis(6-(2H-benzotriazol-2-yl)-4-(1,1,3,3-tetramethylbutyl)phenol), which has the chemical structural formula

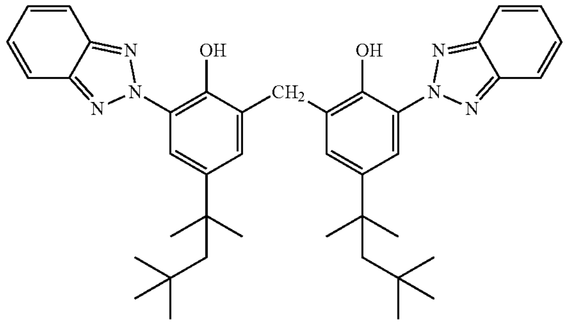 [SMILES: CC(C)(C)CC(C)(C)c1cc(Cc2cc(C(C)(C)CC(C)(C)C)cc(-n3nc4ccccc4n3)c2O)c(O)c(-n2nc3ccccc3n2)c1]

(INCI: bisoctyltriazole). It is obtainable under the proprietary name Tinosorb® from CIBA-Chemikalien GmbH and is distinguished by good UV absorption properties. The disadvantage of this substance is the characteristic of forming imperceptibly thin films on the skin which have unpleasant tactile properties.

In some embodiments, the UV filter compound is a benzotriazole compound having the structure

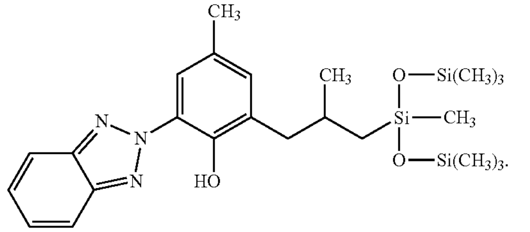

The cosmetic or dermatological compositions can include an additional photoactive compound. In some embodiments, the additional photoactive compound is selected from the group consisting of p-aminobenzoic acid and salts and derivatives thereof; anthranilate and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naptholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxdydiphenyldisulfonate and salts and derivatives thereof; coumarin and derivatives thereof; diazole derivatives; quinine derivatives and salts thereof; quinoline derivatives; hydroxyl-substituted benzophenone derivatives; naphthalate derivatives; methoxy-substituted benzophenone derivatives; uric acid derivatives; vilouric acid derivatives; tannic acid and derivatives thereof; hydroquinone; benzophenone derivatives; 1,3,5-triazine derivatives; phenyldibenzimidazole tetrasulfonate and salts and derivatives thereof; terephthalyidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts, diethylamino hydroxyl benzoyl and derivatives thereof; and combinations of the foregoing.

The cosmetic or dermatological composition may include a cinnamate ester, such as 2-ethylhexyl p-methoxycinnamate, isoamyl p-methoxycinnamate, and a combination thereof. For example, the cinnamate ester can be 2-ethylhexyl p-methoxycinnamate. In some of these embodiments, the cinnamate ester is present in the composition in an amount in a range of about 0.1 wt. % to about 15 wt. %, based on the total weight of the composition.

The cosmetic or dermatological composition also may include about 0.1 to about 10 wt. % of a triplet quencher selected from the group consisting of octocrylene, methyl benzylidene camphor, diethylhexyl 2,6-naphthalate, and combinations thereof.

The cosmetic or dermatological composition also may include about 0.1 to about 10 wt. % of a another singlet quencher such as an alkoxy crylene (e.g., ethylhexyl methoxy crylene), as described in U.S. Pat. Nos. 8,075,808; 7,754,191; 7,173,519; 7,597,825; 7,588,702; and 7,959,834; and U.S. Patent Application No. 2009/0246157, a copolymer of adipic acid and neopentyl glycol that is terminated with cyanodiphenyl propenoic acid, and mixtures thereof.

In some embodiments, the another singlet quencher is an alkoxy crylene having formula (IV):

1.

IV

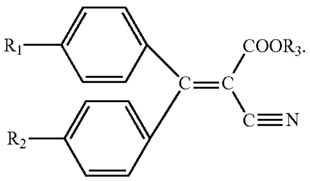

wherein at least one of $R_1$ and $R_2$ is a straight or branched chain $C_1$-$C_{30}$ alkoxy radical, and any non-alkoxy $R_1$ or $R_2$ is hydrogen; and $R_3$ is a straight or branched chain $C_1$-$C_{30}$ alkyl radical.

The cosmetic or dermatological compositions may have conventional additives and solvents that are conventionally used for the treatment, care and cleansing of skin and/or the hair and as a make-up product in decorative cosmetics.

The cosmetic and dermatological compositions described herein can comprise cosmetic auxiliaries such as those conventionally used in such preparations, e.g. preservatives, bactericides, perfumes, antifoams, dyes, pigments which have a coloring effect, thickeners, moisturizers and/or humectants, fats, oils, waxes or other conventional constituents of a cosmetic or dermatological Formulation, such as alcohols, polyols, polymers, foam stabilizers, electrolytes, organic solvents or silicone derivatives.

An additional content of antioxidants is generally preferred. According to the invention, favorable antioxidants which can be used are any antioxidants suitable or conventional for cosmetic and/or dermatological applications.

The antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, .gamma.-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma.-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of gum benzoin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxy-butyro-phenone, uric acid and derivatives thereof, mannose and derivatives thereof, zinc and derivatives thereof (e.g. $ZnO$, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Thus, in some embodiments, the cosmetic or dermatological composition can include one or more oxidation-sensitive or UV-sensitive ingredients selected from the group consisting of retinoid compounds, carotenoid compounds, lipoic acid and derivatives thereof, vitamin E and derivatives thereof, vitamin F and derivatives thereof, and dioic acid in an amount from about 0.0001 wt % to about 10 wt %, based on the total weight of the composition. In particular, the cyano-containing fused tricyclic compounds described herein are very effective at photostabilizing retinoids, coenzyme Q, cholecalciferol, and resveratrol, disclosed in this assignee's U.S. Pat. No. 8,070,989, and U.S. Patent Application Publication Nos. 2012/0114572, 2012/0107255, 2012/0065232, 2011/0251242, and 2011/0142771, hereby incorporated by reference. The cyano-containing fused tricyclic compounds described herein also are effective at photostabilizing protoporphyrin compounds, such as protoporphyrin IX, as previously described herein.

Advantageous hydrophilic active ingredients which (individually or in any combinations with one another) are stabilized by their use together with one or more cyano-containing fused tricyclic compounds include those listed below:

biotin; carnitine and derivatives; creatine and derivatives; folic acid; pyridoxine; niacinamide; polyphenols (in particular flavonoids, very particularly alpha-glucosylrutin); ascorbic acid and derivatives; Hamamelis; Aloe Vera; panthenol; and amino acids.

Particularly advantageous hydrophilic active ingredients for the purposes of the present invention are also water-soluble antioxidants, such as, for example, vitamins.

The amount of hydrophilic active ingredients (one or more compounds) in the preparations is preferably 0.0001 to 10% by weight, particularly preferably 0.001 to 5% by weight, based on the total weight of the preparation.

Particularly advantageous preparations are also obtained when antioxidants are used as additives or active ingredients. According to the invention, the preparations advantageously comprise one or more antioxidants. Favorable, but nevertheless optional antioxidants which may be used are all antioxidants customary or suitable for cosmetic and/or dermatological applications.

The amount of antioxidants (one or more compounds) in the preparations is preferably 0.001 to 30% by weight, particularly preferably 0.05 to 20% by weight, in particular 0.1 to 10% by weight, based on the total weight of the preparation.

If vitamin E and/or derivatives thereof are the antioxidant or antioxidants, it is advantageous to choose their respective concentrations from the range from 0.001 to 10% by weight, based on the total weight of the Formulation.

If vitamin A or vitamin A derivatives, or carotenes or derivatives thereof are the antioxidant or antioxidants, it is advantageous to choose their respective concentrations from the range from 0.001 to 10% by weight, based on the total weight of the Formulation.

It is particularly advantageous when the cosmetic preparations according to the present invention comprise further cosmetic or dermatological active ingredients, preferred active ingredients being antioxidants which can protect the skin against additional oxidative stress.

Advantageous further active ingredients are natural active ingredients and/or derivatives thereof, such as e.g. ubiquinones, retinoids, carotenoids, creatine, taurine and/or β-alanine Formulations according to the invention, which comprise e.g. known antiwrinkle active ingredients, such as flavone glycosides (in particular α-glycosylrutin), coenzyme Q10, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptibility to mechanical stress (e.g. cracking) and the like). In addition, they are advantageously suitable against the appearance of dry or rough skin.

The cosmetic or dermatological compositions can include triazines, benzotriazoles, latex particles, organic pigments, inorganic pigments, and mixtures thereof. In some embodiments, the Preferred particulate UV filter substances for the purposes of the present invention are inorganic pigments, especially metal oxides and/or other metal compounds which are slightly soluble or insoluble in water, especially oxides of titanium ($TiO_2$), zinc ($ZnO$), iron (e.g. $Fe_2O_3$), zirconium ($ZrO_2$), silicon ($SiO_2$), manganese (e.g. $MnO$), aluminum ($Al_2O_3$), cerium (e.g. $Ce_2O_3$), mixed oxides of the corresponding metals, and mixtures of such oxides, and the sulfate of barium ($BaSO_4$).

Zinc oxides for the purposes of the present invention may also be used in the form of commercially available oily or aqueous predispersions Zinc oxide particles and predispersions of zinc oxide particles which are suitable according to the invention are distinguished by a primary particle size of <300 nm and can be obtained under the following proprietary names from the stated companies:

TABLE I

| Proprietary name | Coating | Manufacturer |
|---|---|---|
| Z-Cote HP1 | 2% Dimethicone | BASF |
| Z-Cote | / | BASF |
| ZnO NDM | 5% Dimethicone | H&R |
| ZnO Neutral | / | H&R |
| MZ-300 | / | Tayca Corporation |
| MZ-500 | / | Tayca Corporation |
| MZ-700 | / | Tayca Corporation |
| MZ-303S | 3% Methicone | Tayca Corporation |
| MZ-505S | 5% Methicone | Tayca Corporation |
| MZ-707S | 7% Methicone | Tayca Corporation |
| MZ-303M | 3% Dimethicone | Tayca Corporation |
| MZ-505M | 5% Dimethicone | Tayca Corporation |
| MZ-707M | 7% Dimethicone | Tayca Corporation |
| Z-Sperse Ultra | ZnO (>=56%)/Ethylhexyl Hydroxystearate Benzoate/ Dimethicone/Cyclomethicone | Collaborative Laboratories |
| Samt-UFZO-450/D5 (60%) | ZnO (60%)/Cyclomethicone/ Dimethicone | Miyoshi Kasei |

Particularly preferred zinc oxides for the purposes of the invention are Z-Cote HP1 and Z-Cote from BASF and zinc oxide NDM from Haarmann & Reimer.

Titanium dioxide pigments of the invention may be in the form of both the rutile and anatase crystal modification and may for the purposes of the present invention advantageously be surface-treated ("coated"), the intention being for example to form or retain a hydrophilic, amphiphilic or hydrophobic character. This surface treatment may consist of providing the pigments by processes known per se with a thin hydrophilic and/or hydrophobic inorganic and/or organic layer. The various surface coatings may for the purposes of the present invention also contain water.

Inorganic surface coatings for the purposes of the present invention may consist of aluminum oxide ($Al_2O_3$), aluminum hydroxide $Al(OH)_3$ or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may occur alone, in combination and/or in combination with organic coating materials.

Organic surface coatings for the purposes of the present invention may consist of vegetable or animal aluminum stearate, vegetable or animal stearic acid, lauric acid, dimethylpolysiloxane (also: dimethicones), methylpolysiloxane (methicones), simethicones (a mixture of dimethylpolysiloxane with an average chain length of from 200 to 350 dimethylsiloxane units and silica gel) or alginic acid. These organic surface coatings may occur alone, in combination and/or in combination with inorganic coating materials.

Coated and uncoated titanium dioxides of the invention may be used in the form of commercially available oily or aqueous predispersions. It may be advantageous to add dispersion aids and/or solubilization mediators.

Suitable titanium dioxide particles and predispersions of titanium dioxide particles for the purposes of the present invention are obtainable under the following proprietary names from the stated companies:

| Proprietary name | Coating | Additional ingredients of the predispersion | Manufacturer |
|---|---|---|---|
| MT-150W | None | — | Tayca Corporation |
| MT-150A | None | — | Tayca Corporation |
| MT-500B | None | — | Tayca Corporation |
| MT-600B | None | — | Tayca Corporation |
| MT-100TV | Aluminum hydroxide Stearic acid | — | Tayca Corporation |
| MT-100Z | Aluminum hydroxide Stearic acid | — | Tayca Corporation |
| MT-100T | Aluminum hydroxide Stearic acid | — | Tayca Corporation |
| MT-500T | Aluminum hydroxide Stearic acid | — | Tayca Corporation |
| MT-100S | Aluminum hydroxide Lauric acid | — | Tayca Corporation |
| MT-100F | Stearic acid Iron oxide | — | Tayca Corporation |
| MT-100SA | Alumina Silica | — | Tayca Corporation |
| MT-500SA | Alumina Silica | — | Tayca Corporation |
| MT-600SA | Alumina Silica | — | Tayca Corporation |
| MT-100SAS | Alumina Silica Silicone | — | Tayca Corporation |
| MT-500SAS | Alumina Silica Silicone | — | Tayca Corporation |
| MT-500H | Alumina | — | Tayca Corporation |
| MT-100AQ | Silica Aluminum hydroxide Alginic acid | — | Tayca Corporation |
| Eusolex T | Water Simethicone | — | Merck KgaA |
| Eusolex T-2000 | Alumina Simethicone | — | Merck KgaA |
| Eusolex T-Olio F | Silica Dimethylsilate Water | $C_{12-15}$ Alkylbenzoate Calcium Polyhydroxystearate Silica Dimethylsilate | Merck KgaA |
| Eusolex T-Olio P | Water Simethicone | Octyl Palmitate PEG-7 Hydrogenated Castor Oil Sorbitan Oleate Hydrogenated Castor Oil Beeswax Stearic acid | Merck KgaA |
| Eusolex T-Aqua | Water Alumina Sodium metaphosphate | Phenoxyethanol Sodium Methylparabens | Merck KgaA |

-continued

| Proprietary name | Coating | Additional ingredients of the predispersion | Manufacturer |
|---|---|---|---|
| Eusolex T-45D | Alumina Simethicone | Sodium metaphosphate Isononyl Isononanuate Polyglyceryl Ricinoleate | Merck KgaA |
| Kronos 1171 (Titanium dioxide 171) | None | — | Kronos |
| Titanium dioxide P25 | None | — | Degussa |
| Titanium dioxide T805 | Octyltri-methylsilane (Uvinul $TiO_2$) | — | Degussa |
| UV-Titan X610 | Alumina Dimethicone | — | Kemira |
| UV-Titan X170 | Alumina Dimethicone | — | Kemira |
| UV-Titan X161 | Alumina Silica Stearic acid | — | Kemira |
| UV-Titan M210 | Alumina | — | Kemira |
| UV-Titan M212 | Alumina | Glycerol ` | Kemira |
| UV-Titan M262 | Alumina Silicone | — | Kemira |
| UV-Titan M160 | Alumina Silica Stearic acid | — | Kemira |
| Tioveil AQ 10PG | Alumina Silica | Water Propylene glycol | Solaveil Uniquema |
| Mirasun TiW 60 | Alumina Silica | Water | Rhone-Poulenc |

Preferred titanium dioxides are distinguished by a primary particle size between 10 nm to 150 nm Titanium dioxides particularly preferred for the purposes of the present invention are MT-100 Z and MT-100 TV from Tayca Corporation, Eusolex T-2000 from Merck and titanium dioxide T 805 from Degussa.

Further advantageous pigments are latex particles. Latex particles which are advantageous according to the invention are described in the following publications: U.S. Pat. No. 5,663,213 and EP 0 761 201. Particularly advantageous latex particles are those formed from water and styrene/acrylate copolymers and available for example under the proprietary name "Alliance SunSphere" from Rohm & Haas.

An advantageous organic pigment for the purposes of the present invention is 2,2'-methylenebis(6-(2H-benzotriazol-2-yl)-4-(1,1,3,3-tetramethylbutyl-)phenol) (INCI: bis-octyl-triazol), which is obtainable under the proprietary name Tinosorb® M from CIBA-Chemikalien GmbH.

EXAMPLES

Comparison of abilities of cyano-containing fused tricyclic compounds to photostabilize Avobenzone and the combination of oxyymethoxy cinnamate (OMC) and Avobenzone, in comparison to the ethylhexyl methoxycrylene of U.S. Pat. Nos. 8,075,808; 7,754,191; 7,173,519; 7,597,825; 7,588,702; and 7,959,834; and U.S. Patent Application No. 2009/0246157.

Y-1-9=Ethylhexyl cyano xanthenylidene acetate

Y-1-15=Ethylhexyl cyano thioxanthenylidene acetate

Y-1-22=Ethylhexyl dimethyl 2,2'-anthracene-9,10-diylidenebis(cyanoacetate)

APB072707F=Isopropyl cyano fluorenylidene acetate

Experiment 1 compares the cyano-containing fused tricyclic compounds at 3% (w/w) to photostabilize 3% Avobenzone, except for A6, which brings Y-1-22 up to the same molar concentration as the others when they're at 3%. The results as shown in Table I are graphically in FIG. 1.

TABLE I

| Experiment 1 (JZ5-124A), 20 uls solution on quartz | | | | | | | |
|---|---|---|---|---|---|---|---|
| Sample ID | A1 | A2 | A3 | A4 | A5 | A6 | A7 |
| Y-1-9 | | 0.30 | | | | | |
| Y-1-15 | | | 0.30 | | | | |
| Y-1-22 | | | | 0.30 | | 0.45 | |
| SolaStay S1 | | | | | 0.30 | | |
| ABP072707F | | | | | | | 0.30 |
| Avobenzone | 0.30 | 0.30 | 0.30 | 0.30 | 0.30 | 0.30 | 0.30 |
| PA 18 | 0.20 | 0.20 | 0.20 | 0.20 | 0.20 | 0.20 | 0.20 |
| C12-15 alkyl benzoate | 2.00 | 1.70 | 1.70 | 1.70 | 1.70 | 1.55 | 1.70 |
| Ethyl acetate | 7.50 | 7.50 | 7.50 | 7.50 | 7.50 | 7.50 | 7.50 |
| Total | 10.00 | 10.00 | 10.00 | 10.00 | 10.00 | 10.00 | 10.00 |
| % UVB remaining, quartz, 10med | 71.1 | 99.0 | 99.8 | 97.3 | 96.7 | 99.0 | 92.9 |
| % UVA remaining, quartz, 10med | 26.2 | 95.9 | 94.7 | 91.6 | 97.3 | 96.7 | 94.6 |

* SolaStay S1 - ethylhexyl methoxycrylene

Figure 2:
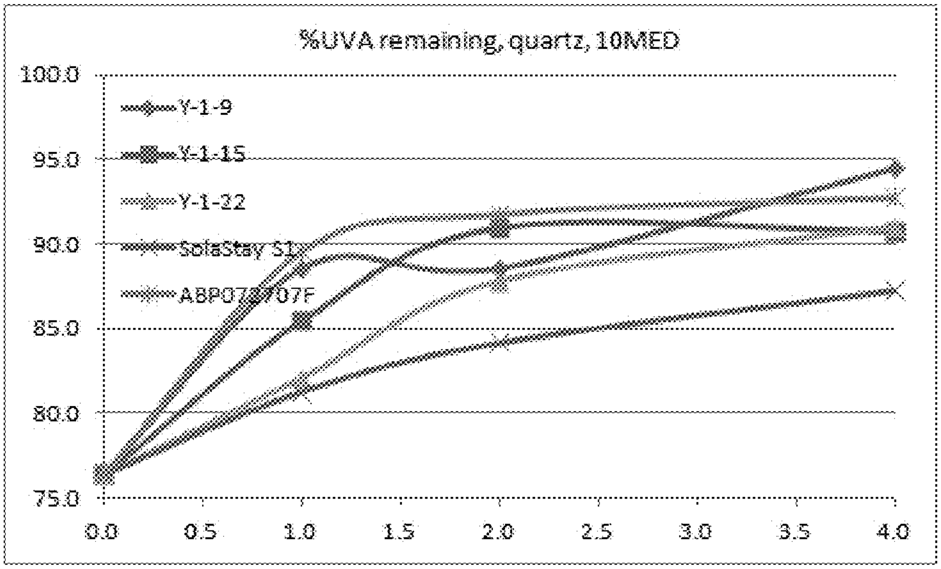
FIG. 2 is a graph showing the superior ability of cyano-containing fused tricyclic compounds to photostabilize a combination of Avobenzone and octylmethoxy cinnamate (OMC) in comparison to the ethylhexyl methoxycrylene of this Assignee's U.S. Pat. Nos. 8,075,808; 7,754,191; 7,173,519; 7,597,825; 7,588,702; and 7,959,834; and U.S. Patent Application No. 2009/0246157.

Experiment 2 compares the compounds at 3% to photostabilize Avobenzone at 3% and OMC at 7.5%. The results are shown in Table II and graphically in FIG. 2.

TABLE II

| Experiment 2, 20ul on quartz, 10MED | | | | | |
|---|---|---|---|---|---|
| | Y-1-9 | Y-1-15 | Y-1-22 | SolaStay S1 | ABP072707F |
| % UVB | | | | | |
| 0.0 | 84.7 | 84.7 | 84.7 | 84.7 | 84.7 |
| 1.0 | 91.8 | 90.0 | 87.8 | 87.8 | 93.3 |
| 2.0 | 91.1 | 93.8 | 92.1 | 90.1 | 93.7 |
| 4.0 | 95.3 | 93.9 | 94.7 | 91.5 | 94.2 |

TABLE II-continued

| Experiment 2, 20ul on quartz, 10MED | | | | | |
|---|---|---|---|---|---|
| | Y-1-9 | Y-1-15 | Y-1-22 | SolaStay S1 | ABP072707F |
| % UVA | | | | | |
| 0.0 | 76.4 | 76.4 | 76.4 | 76.4 | 76.4 |
| 1.0 | 88.6 | 85.5 | 82.1 | 81.3 | 89.6 |
| 2.0 | 88.6 | 91.0 | 87.8 | 84.2 | 91.8 |
| 4.0 | 94.5 | 90.8 | 91.0 | 87.3 | 92.8 |

The invention claimed is:

1. A photostabilized photoactive composition comprising a mixture of a photoactive compound that develops a singlet excited state, or fluoresces when subjected to UV radiation and an effective amount of an excited state quencher comprising a cyano-containing fused tricyclic compound of formula (I):

(I)

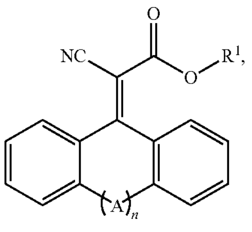

wherein:

A is selected from the group consisting of O, S, C═O, and

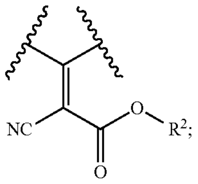

n is 1; and, $R^1$ and $R^2$ are each independently selected from the group consisting of alkyl, cycloalkyl, ether, aryl, and amino.

2. The photostabilized photoactive composition of claim 1, wherein the cyano-containing fused tricyclic compound of Formula I is selected from the group consisting of:

Formula Ib

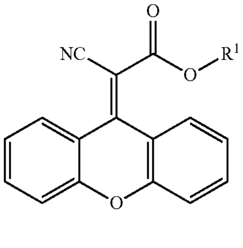

-continued

Formula Ic

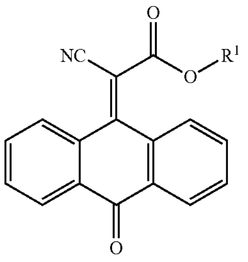

Formula Id

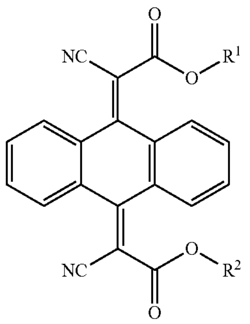

Formula Ie

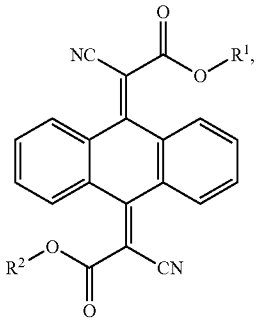

and

Formula If

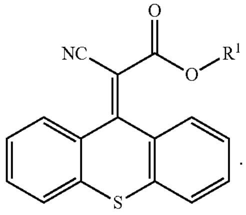

.

3. The photostabilized photoactive composition of 2, wherein $R^1$ and $R^2$ are each independently $C_1$-$C_{30}$ alkyl.

4. The photostabilized photoactive composition of claim 3, wherein $R^1$ and $R^2$ are each independently $C_1$-$C_{20}$ alkyl.

5. The photostabilized photoactive composition of claim 4, wherein $R^1$ and $R^2$ are each independently $C_1$-$C_{10}$ alkyl.

6. The photostabilized photoactive composition of claim 5, wherein $R^1$ and $R^2$ are each independently methyl, ethyl, propyl, isopropyl, or 2-ethylhexyl.

7. The photostabilized photoactive composition of claim 6, wherein the compound of Formula I is selected from the group consisting of:

Formula Iai

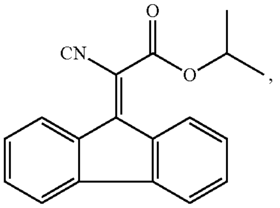

Formula Ibi

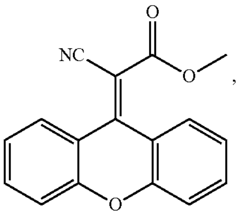

Formula Ici

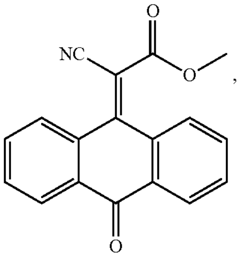

Formula Idi

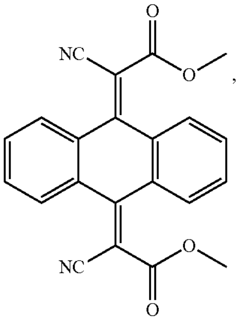

Formula Iei

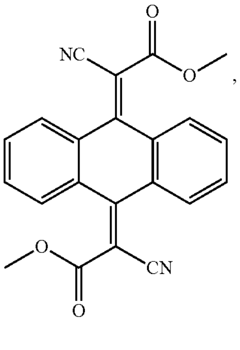

and

Formula Ifi

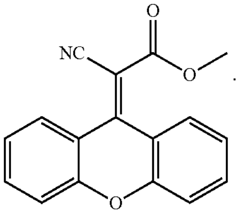

8. The photostabilized photoactive composition of claim 1, wherein the compound of formula (I) is present in an amount in the weight range of 0.1% to 20%, based on the total weight of the composition.

9. The photostabilized photoactive composition of claim 8, wherein the compound of formula (I) is present in an amount in the weight range of 1% to 10%, based on the total weight of the composition.

10. The photostabilized photoactive composition of claim 1, wherein the photoactive compound is selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naptholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxdydiphenyldisulfonate and salts and derivatives thereof; coumarin and derivatives thereof; diazole derivatives; quinine derivatives and salts thereof; quinoline derivatives; hydroxyl-substituted benzophenone derivatives; naphthalate derivatives; methoxy-substituted benzophenone derivatives; uric acid derivatives; vilouric acid derivatives; tannic acid and derivatives thereof; hydroquinone; benzophenone derivatives; 1,3,5-triazine derivatives; disodium phenyl dibenzimidazole and salts thereof; terephthalyidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts, diethylamino hydroxyl benzoyl and derivatives thereof; phenylbenzimidazole sulfonic acid and salts thereof; terephthalylidene dicamphor sulfonic acid and salts thereof; and combinations of the foregoing.

11. The photostabilized photoactive composition of claim 1, wherein the photoactive compound comprises a dibenzoylmethane derivative.

12. The photostabilized photoactive composition of claim 10, further including a cinnamate ester.

13. The photostabilized photoactive composition of claim 12, wherein the cinnamate ester is an ester of an alkoxycinnamate.

14. The photostabilized photoactive composition of claim 13, wherein the alkoxycinnamate ester is a methoxycinnamate ester.

15. The photostabilized photoactive composition of claim 12, wherein the cinnamate ester is selected from the group consisting of 2-ethylhexyl p-methoxycinnamate, isoamyl p-methoxycinnamate, and a combination thereof.

16. The photostabilized photoactive composition of claim 13 wherein the cinnamate ester is 2-ethylhexyl p-methoxycinnamate.

17. The photostabilized photoactive composition of claim 11, wherein the dibenzoylmethane derivative comprises butylmethoxy dibenzoylmethane.

18. The photostabilized photoactive composition of claim 1, further including a naphthalene dicarboxylic acid ester in an amount of 0.1 to 10 wt %.

19. The photostabilized photoactive composition of claim 18, wherein the naphthalene dicarboxylic acid ester comprises a diethylhexyl 2,6-naphthalene dicarboxylic acid ester.

20. The photostabilized photoactive composition of claim 1, further including a salicylate or a derivative thereof in an amount of 0.1 to 10 wt %.

21. The photostabilized photoactive composition of claim 15, further including a salicylate or a derivative thereof in an amount of 0.1 to 10 wt %.

22. The photostabilized photoactive composition of claim 1, further including a benzophenone or a derivative thereof in an amount of 0.1 to 10 wt. %.

23. The photostabilized photoactive composition of claim 22, wherein the benzophenone comprises benzophenone-3 in an amount of 0.1 to 10 wt. %.

24. The photostabilized photoactive composition of claim 1, wherein the photoactive compound comprises a 1,3,5-triazine derivative.

25. The photostabilized photoactive composition of claim 1, wherein the photoactive compound comprises 2-(methylbenzilidene)-camphor.

26. The photostabilized photoactive composition of claim 1, wherein the photoactive compound comprises a dibenzoylmethane derivative selected from the group consisting of 2-methyldibenzoylmethane; 4-methyldibenzoylmethane; 4-isopropyldibenzoylmethane; 4-tert-butyldibenzoylmethane; 2,4-dimethydibenzoylmethane; 2-5-dimethydibenzoylmethane; 4,4'-diispropyldibenzoylmethane; 4,4'-dimethoxydibenzoylmethane; 4-tert-butyl-4'-methoxdibenzoylmethane; 2-methyl-5-isopropy-4'-methoxydibenzoylmethane; 2-methyl-5-tert-butyl-4'-methoxydibenzoylmethane; 2,4-dimethyl-4'-methoxydibenzoymethane; 2,6-dimethyl-4-tert-butyl-4'-methoxydibenzolmethane, and combinations thereof.

27. The photostabilized photoactive composition of claim 1 further including 0.1 to 10 wt. % of a triplet quencher selected from the group consisting of octocrylene, methyl benzylidene camphor, diethylhexyl 2,6-naphthalate, diethylhexyl syringylidene malonate, and combinations thereof.

28. The photostabilized photoactive composition of claim 1 further comprising 0.1 to 10 wt. % benzophenone-3.

29. The photostabilized photoactive composition of claim 1 further comprising 0.1 to 10 wt. % octyl salicylate.

30. The photostabilized photoactive composition of claim 1, wherein the composition includes a compound selected from the group consisting of methylene bis-benzotriazolyl tetranl ethylbutylphenol, salts and derivatives thereof; bis-ethylhexyloxyphenol methoxyphenyl triazine, and salts and derivatives thereof.

31. The photostabilized photoactive composition of claim 1, wherein the composition includes a hydroxyl-substituted benzophenone derivative or a methoxy-substituted benzophenone derivative, or a combination thereof.

32. The photostabilized photoactive composition of claim 1, further comprising a diester or polyester of naphthalene dicarboxylic acid selected from the group consisting of compounds of formula (II) and (III), and combinations thereof:

(II)

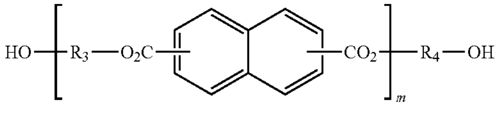

(III)

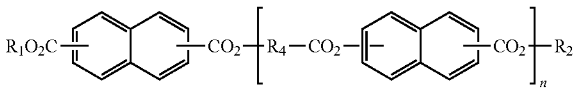

wherein $R_1$ and $R_2$ are the same or different and selected from the group consisting of $C_1$-$C_{22}$ alkyl groups, dials having the structure $HO—R_4—OH$, and polyglycols having the structure $HO—R_3—(—O—R_4—)_n—OH$; wherein each $R_3$ and $R_4$ is the same or different and selected from the group consisting of $C_1$-$C_6$ straight or branched chain alkyl groups; and wherein m and n are each in a range of 1 to 100.

33. The photostabilized photoactive composition of claim 32, comprising a diester of formula (III) wherein R1 and R2 are 2-ethylhexyl.

34. The photostabilized photoactive composition of claim 1 further including about 0.1 wt. % to about 10 wt. % of another singlet quencher.

35. The photostabilized photoactive composition of claim 34, wherein the another singlet quencher is an alkoxy crylene having formula (IV):

(IV)

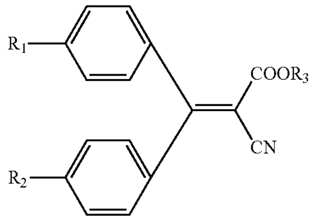

wherein at least one of $R_1$ and $R_2$ is a straight or branched chain $C_1$-$C_{30}$ alkoxy radical, and any non-alkoxy $R_1$ or $R_2$ is hydrogen; and $R_3$ is a straight or branched chain $C_1$-$C_{30}$ alkyl radical.

36. The photostabilized photoactive composition of claim 1, wherein said mixture includes a cosmetically acceptable carrier.

37. The photostabilized photoactive composition of claim 1, wherein said mixture includes an oil phase having a dielectric constant of at least about 8.

38. A method of increasing the UV absorbing life of a composition containing (a) a dibenzoylmethane derivative and/or (b) a cinnamate ester comprising adding a compound of formula (I) in an amount effective to prevent the reaction of (a) with (b); or to photostabilize (a) and/or (b)

(I)

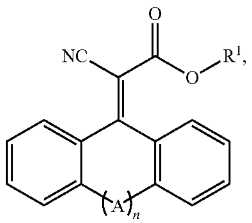

wherein:

A is selected from the group consisting of O, S, C═O, and

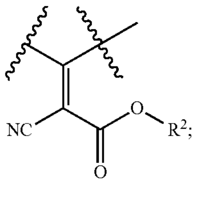

n is 1; and, $R^a$ is hydrogen or $C_1$-$C_{10}$ alkyl.

39. The method of claim 38, wherein the compound of formula (I) is selected from the group consisting of:

Formula Ia

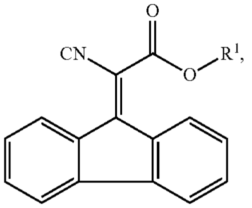

Formula Ib

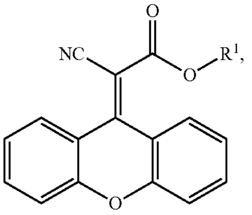

Formula Ic

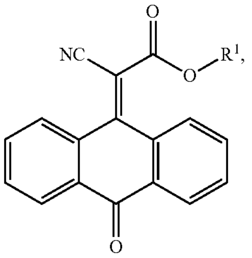

Formula Id

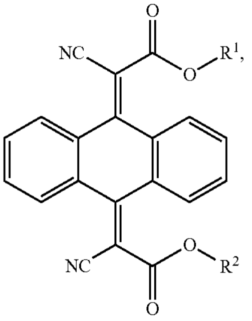

Formula Ie

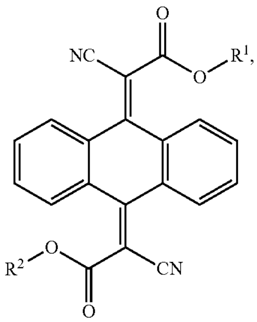

and

Formula If

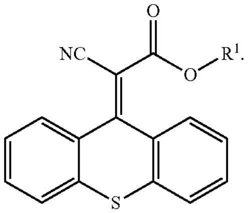

wherein $R^1$ and $R^2$ are each independently selected from the group consisting of alkyl, cycloalkyl, ether, aryl, and amino.

40. The method of claim 39, wherein $R^1$ and $R^2$ are each independently $C_1$-$C_{30}$ alkyl.

41. The method of claim 40, wherein $R^1$ and $R^2$ are each independently $C_1$-$C_{20}$ alkyl.

42. The method of claim 41, wherein $R^1$ and $R^2$ are each independently $C_1$-$C_{10}$ alkyl.

43. The method of claim 42, wherein $R^1$ and $R^2$ are each independently methyl, ethyl, propyl, isopropyl, or 2-ethylhexyl.

44. The method of claim 43, wherein the compound of Formula I is selected from the group consisting of:

Formula Iai

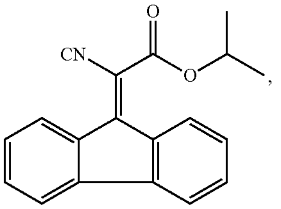

Formula Ibi

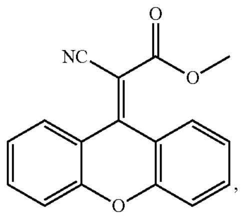

Formula Ici

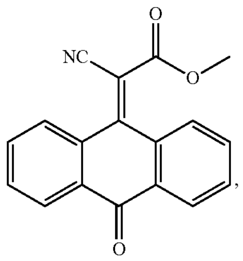

Formula Idi

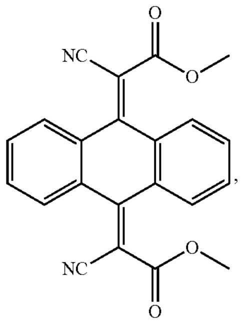

-continued

Formula Iei

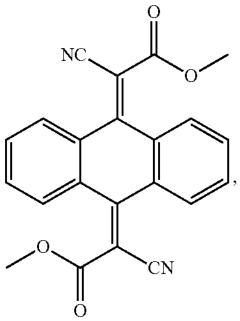

, and

Formula Ifi

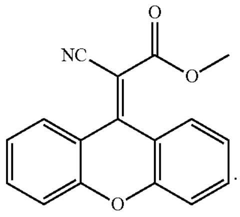

.

45. The method of claim 38, wherein the compound of formula (I) is present in an amount in the weight range of 0.1% to 20%, based on the total weight of the composition.

46. The method of claim 45, wherein the compound of formula (I) is present in an amount in the weight range of 3% to 10%, based on the total weight of the composition.

47. The method of claim 38, further comprising a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naptholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxdydiphenyldisulfonate and salts and derivatives thereof; coumarin and derivatives thereof; diazole derivatives; quinine derivatives and salts thereof; quinoline derivatives; hydroxyl-substituted benzophenone derivatives; naphthalate derivatives; methoxy-substituted benzophenone derivatives; uric acid derivatives; vilouric acid derivatives; tannic acid and derivatives thereof; hydroquinone; benzophenone derivatives; 1,3,5-triazine derivatives; disodium phenyl dibenzimidazole and salts thereof; terephthalyidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts, diethylamino hydroxyl benzoyl and derivatives thereof; phenylbenzimidazole sulfonic acid and salts thereof; terephthalylidene dicamphor sulfonic acid and salts thereof; and combinations of the foregoing.

48. The method of claim 38, wherein the photoactive compound comprises a dibenzoylmethane derivative.

49. The method of claim 48, wherein the photoactive compound comprises a cinnamate ester.

50. The method of claim 38, wherein the composition includes a hydroxyl-substituted benzophenone derivative or a methoxy-substituted benzophenone derivative, or a combination thereof.

51. The method of claim 38, wherein the composition includes about 0.1 wt. % to about 10 wt. % of another singlet quencher.

52. The method of claim 51, wherein the another singlet quencher is an alkoxy crylene having formula (IV):

(IV)

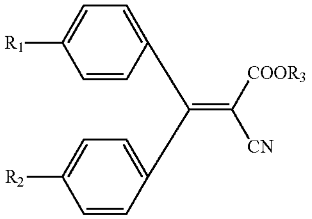

wherein at least one of $R_1$ and $R_2$ is a straight or branched chain $C_1$-$C_{30}$ alkoxy radical, and any non-alkoxy $R_1$ or $R_2$ is hydrogen; and $R_3$ is a straight or branched chain $C_1$-$C_{30}$ alkyl radical.

53. A composition comprising a mixture of a photoactive compound that reaches an excited state when exposed to UV radiation from UV-induced photodegradation and an effective amount of an excited state quencher comprising a cyano-containing fused tricyclic compound of formula (I):

(I)

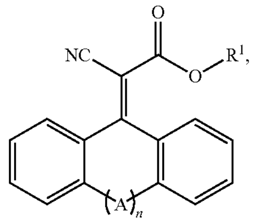

wherein:

A is selected from the group consisting of O, S, C═O, and

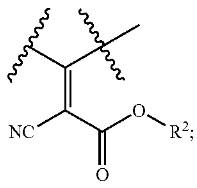

n is 1; and, $R^1$ and $R^2$ are each independently selected from the group consisting of alkyl, cycloalkyl, ether, aryl, and amino, wherein the photoactive compound is selected from the group consisting of retinoids, coenzyme Q, cholecalciferol, resveratrol, protoporphyrins, and combinations thereof.

54. The photostabilized photoactive composition of claim 53, wherein the protoporphyrin comprises protoporphyrin IX.

55. A method of protecting a photoactive compound that reaches an excited state when exposed to UV radiation from UV-induced photodegradation in a composition containing said photoactive compound, comprising: combining with said photoactive compound a cyano-containing fused tricyclic compound of formula (I):

(I)

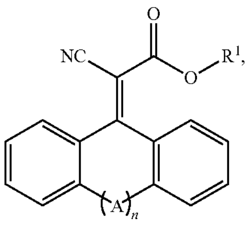

wherein:

A is selected from the group consisting of O, S, C═O, and

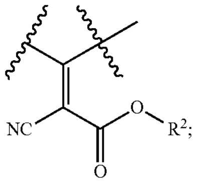

n is 1; and, $R^1$ and $R^2$ are each independently selected from the group consisting of alkyl, cycloalkyl, ether, aryl, and amino, wherein the photoactive compound is selected from the group consisting of retinoids, coenzyme Q, cholecalciferol, resveratrol, protoporphyrins, and combinations thereof.

56. The method of claim 55, wherein the protoporphyrin comprises protoporphyrin IX.

* * * * *